(12) United States Patent
Angel et al.

(10) Patent No.: US 6,939,323 B2
(45) Date of Patent: Sep. 6, 2005

(54) NEEDLELESS INJECTOR

(75) Inventors: Aimee B. Angel, Atherton, CA (US); Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/200,574

(22) Filed: Jul. 19, 2002

(65) Prior Publication Data

US 2003/0083611 A1 May 1, 2003

Related U.S. Application Data

(60) Provisional application No. 60/338,169, filed on Oct. 26, 2001.

(51) Int. Cl.[7] .......................... A61M 5/20; F01B 29/10; F02G 1/04
(52) U.S. Cl. ........................................ 604/134; 60/528
(58) Field of Search .............................. 604/48, 68, 69, 604/70, 71, 72, 73, 131, 134, 181, 187; 60/527, 528

(56) References Cited

U.S. PATENT DOCUMENTS

| 3,057,349 A | | 10/1962 | Ismach |
| 3,659,600 A | * | 5/1972 | Merrill ..................... 604/891.1 |
| 3,815,594 A | | 6/1974 | Doherty |

(Continued)

FOREIGN PATENT DOCUMENTS

| EP | 0 599 940 B1 | 12/1997 |
| EP | 0 834 330 A2 | 4/1998 |
| EP | 1 020 200 A2 | 7/2000 |
| EP | 0 710 310 B1 | 12/2000 |
| GB | 686343 | 1/1953 |
| JP | 06327639 | 1/1994 |
| JP | 6-327639 | 11/1994 |
| JP | 01046344 | 1/2001 |
| JP | P2001-46344 A | 2/2001 |
| WO | WO 00/23132 | 4/2001 |
| WO | WO 01/26716 A1 | 4/2001 |
| WO | WO 01/37907 A1 | 5/2001 |
| WO | WO 02/100469 A2 | 12/2002 |

OTHER PUBLICATIONS

Diridollou, S., "Sex– and site–dependent variations in the thickness and mechanical properties of human in vivo," *International Journal of Cosmetic Science* 22:421–435 (2000).

He, M.M., et al., "Two–Exponential Rheological Models of the Mechanical Properties of the Stratum Corneum," *Pharmaceutical Research* 13:S1–S604 (1996).

Manschot, J.F.M. and Brakkee, A.J.M., "The Measurement and Modelling of the Mechanical Properties of Human Skin In Vivo–I. The Measurements," *J. Biomech.* 19(7):511–515 (1986).

(Continued)

*Primary Examiner*—Nicholas Luccheshi
*Assistant Examiner*—Mark K. Han
(74) *Attorney, Agent, or Firm*—Hamilton, Brook, Smith & Reynolds, P.C.

(57) ABSTRACT

An injector includes a housing having a chamber for holding a liquid formulation of an active principle to be injected into a biological body and an output port in fluid communication with the chamber through which the liquid formulation is injected. A piston is positioned within the housing, and includes an end portion with substantially the same shape as the chamber. A magnetic force draws the piston and housing together to expel the liquid formulation out of the chamber through the output port.

32 Claims, 2 Drawing Sheets

U.S. PATENT DOCUMENTS

| | | | |
|---|---|---|---|
| 3,977,402 A | | 8/1976 | Pike |
| 4,108,177 A | | 8/1978 | Pistor |
| 4,206,769 A | | 6/1980 | Dikstein |
| 4,435,173 A | | 3/1984 | Siposs et al. |
| 4,447,225 A | * | 5/1984 | Taff et al. ............ 604/71 |
| 4,744,841 A | | 5/1988 | Thomas |
| 4,777,599 A | | 10/1988 | Dorogi et al. |
| 4,886,499 A | | 12/1989 | Cirelli et al. |
| 5,092,901 A | | 3/1992 | Hunter et al. |
| 5,116,313 A | | 5/1992 | McGregor |
| 5,354,273 A | | 10/1994 | Hagen |
| 5,405,614 A | | 4/1995 | D'Angelo et al. |
| 5,480,381 A | | 1/1996 | Weston |
| 5,505,697 A | | 4/1996 | McKinnon, Jr. et al. |
| 5,622,482 A | | 4/1997 | Lee |
| 5,694,920 A | | 12/1997 | Abrams et al. |
| 5,722,953 A | | 3/1998 | Schiff et al. |
| 5,840,062 A | | 11/1998 | Gumaste et al. |
| 5,919,167 A | | 7/1999 | Mulhauser et al. |
| 6,004,287 A | | 12/1999 | Loomis et al. |
| 6,037,682 A | | 3/2000 | Shoop et al. |
| 6,056,716 A | | 5/2000 | D'Antonio et al. |
| 6,074,360 A | | 6/2000 | Haar et al. |
| 6,123,684 A | * | 9/2000 | Deboer et al. ............ 604/68 |
| 6,203,521 B1 | | 3/2001 | Menne et al. |
| 6,258,062 B1 | | 7/2001 | Thielen et al. |
| 6,272,857 B1 | | 8/2001 | Varma |
| 6,375,624 B1 | | 4/2002 | Uber, III et al. |
| 6,408,204 B1 | | 6/2002 | Hirschman |

OTHER PUBLICATIONS

Zhang, M. and Roberts, V.C., "The effect of shear forces externally applied to skin surface on underlying tissues," *J. Biomed. Eng.* 15:451–456 (1993).

Reihsner, R., et al., "Two–dimensional elastic properties of human skin in terms of an incremental model at the in vivo configuration," *Med. Eng. Phys.* 17(4):304–313 (1995).

Hirota, F.G., et al., "An Implicit Finite Element Method for Elastic Solids in Contact," *IEEE*:136–146 (2001).

Menciassi, A., et al., "An Instrumented Probe for Mechanical Characterization of Soft Tissues," *Biomedical Microdevices* 3(2):149–156 (2001).

Soong, T.T. and Huang, W.N., "A Stochastic Model for Biological Tissue Elasticity," Proceedings of the Fourth Canadian Congress of Applied Mechanics, Montreal, Canada (1973).

Bischoff, J.E., et al., "Finite element modeling of human skin using an isotropic, nonlinear elastic constitutive model," *Journal of Biomechanics* 33:645–652 (2000).

Flynn, D.M., et al., "A Finite Element Based Method to Determine the Properties of Planar Soft Tissue," *Journal of Biomechanical Engineering* 120 (2):202–210 (1998).

Oka, H. and Irie, T., "Mechanical impedance of layered tissue," *Medical Progress through Technology, Supplement to* vol. 21:1–4 (1997).

Lindahl, O.A., et al., "A tactile sensor for detection of physical properties of human skin in vivo," *Journal of Medical Engineering & Technology,* 22(4):147–153 (1998).

Patton, R.L., "Mechanical Compliance Transfer Function Analysis for Early Detection of Pressure Ulcers." Unpublished master's thesis, Massachusetts Institute of Technology, Cambridge, MA. (1999).

Korenberg, M.J. and Hunter, I.W., "The Identification of Nonlinear Biological Systems: Volterra Kernel Approaches," *Annals of Biomedical Engineering,* 24:250–268 (1996).

Manschot, J.F.M. and Brakkee, A.J.M., "The Measurement and Modelling of the Mechanical Properties of Human Skin In Vivo–II. The Model," *J. Biomechanics* 19(7):517–521 (1986).

* cited by examiner

NEEDLELESS INJECTOR

RELATED APPLICATION

This application claims the benefit of U.S. Provisional Application No. 60/338,169, filed Oct. 26, 2001, the entire contents of which are incorporated herein by reference.

BACKGROUND

Injection of a liquid such as a drug into a human patient or an agriculture animal is performed in a number of ways. One of the easiest methods for drug delivery is through the skin which is the outermost protective layer of the body. It is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue. It extends around 10–20 microns from the skin surface and has no blood supply. Because of the density of this layer of cells, moving compounds across the skin, either into or out of the body, can be very difficult.

The current technology for delivering local pharmaceuticals through the skin includes methods that use needles or other skin piercing devices. Invasive procedures, such as use of needles or lances, effectively overcome the barrier function of the stratum corneum. However, these methods suffer from several major disadvantages: local skin damage, bleeding, and risk of infection at the injection site, and creation of contaminated needles or lances that must be disposed of. Further, when these devices are used to inject drugs in agriculture animals, the needles break off from time to time and remain embedded in the animal.

Thus, it would be advantageous to be able to inject small, precise volumes of pharmaceuticals quickly through the skin without the potential of a needle breaking off in the animal.

SUMMARY

Some have proposed using needleless devices to effectively deliver drugs to a biological body. For example, in some of these proposed devices, pressurized gas is used to expel a drug from a chamber into the body. In another device, a cocked spring is released which then imparts a force on a chamber to expel the drug. In these types of devices, however, the pressure applied to the drug decreases as the gas expands or the spring extends. It is desirable, however, for the injection pressure to remain the same or increase during the injection period.

In one aspect of the invention, an injector includes a housing having a chamber for holding a liquid formulation of an active principle to be injected into a biological body and an output port in fluid communication with the chamber through which the liquid formulation is injected. A piston is positioned within the housing, and includes an end portion with substantially the same shape as the chamber. A magnetic force draws the piston and housing together to expel the liquid formulation out of the chamber through the output port.

Embodiments of this aspect can include one or more of the following features. The output port can has a diameter of approximately 50 μm to 200 μm, and the chamber can have a tapered shape. The injector includes an inlet port for filling the chamber with the liquid formulation. The injector includes an actuator attached to the piston and made of shape memory alloy. The actuator moves the piston away from the housing when a potential is applied to the actuator. When the potential is removed the piston moves towards the housing. The actuator is a fiber of the shape memory alloy, and the shape memory alloy can be Ni—Ti. The shape memory alloy is approximately 10 mm to 200 mm long, and it contracts approximately 0.5 mm to 10 mm when the potential is applied to the alloy. The shape memory alloy structure changes phase from martensite to austenite when the potential is applied to the alloy.

In some embodiments, the injector includes a capacitor that applies the potential when it discharges. The capacitor has an energy output of at least 10 J and can be approximately 100 J.

The injector has an injection pressure of at least 1 MPa and a maximum injection pressure of approximately 300 MPa. In certain embodiments, the injector has a cycle time of about one sec.

In another aspect of the invention, an actuator includes a contracting material under tension produced by a magnetic force, and a capacitor which is able to discharge a potential to the fiber to cause the fiber to contract. The fiber relaxes to a stretched state when the potential is removed. The contracting material can be a shape memory alloy or a contracting polymer or polymers, or any other suitable contracting material.

In yet another aspect of the invention, a injector includes a housing having a chamber for holding a liquid formulation of an active principle to be injected into a biological body, and an output port in fluid communication with the chamber through which the liquid formulation is injected. A piston is positioned within the housing, and includes an end portion with substantially the same shape as the chamber. An actuator is attached to the piston and made of shape memory alloy. The piston and housing are drawn together by a magnetic force, and the actuator moves the piston away from the housing when a potential is applied to the actuator, and the piston moves towards the housing when the voltage is removed to expel the liquid formulation out of the chamber through the output port.

Related aspects of the invention include a method of injecting a liquid formulation of an active principle into a biological body with an injector having one or more of the aforementioned features, and a method of actuating a fiber of shape memory alloy.

Embodiments of this invention can have one or more of the following advantages. The injector is self-contained and portable. Since the injection process is needleless, there are no needles that can break off and remain within the biological body. Since the injector can be re-charged at a rapid rate, a large number of animals can be injected with the liquid formulation over a short period of time. Further, since the injector contains enough liquid formulation for numerous injections, the operator is able to inject many animals with a single injector before refilling a reservoir or a set of reservoirs or obtaining another injector with a filled reservoir.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
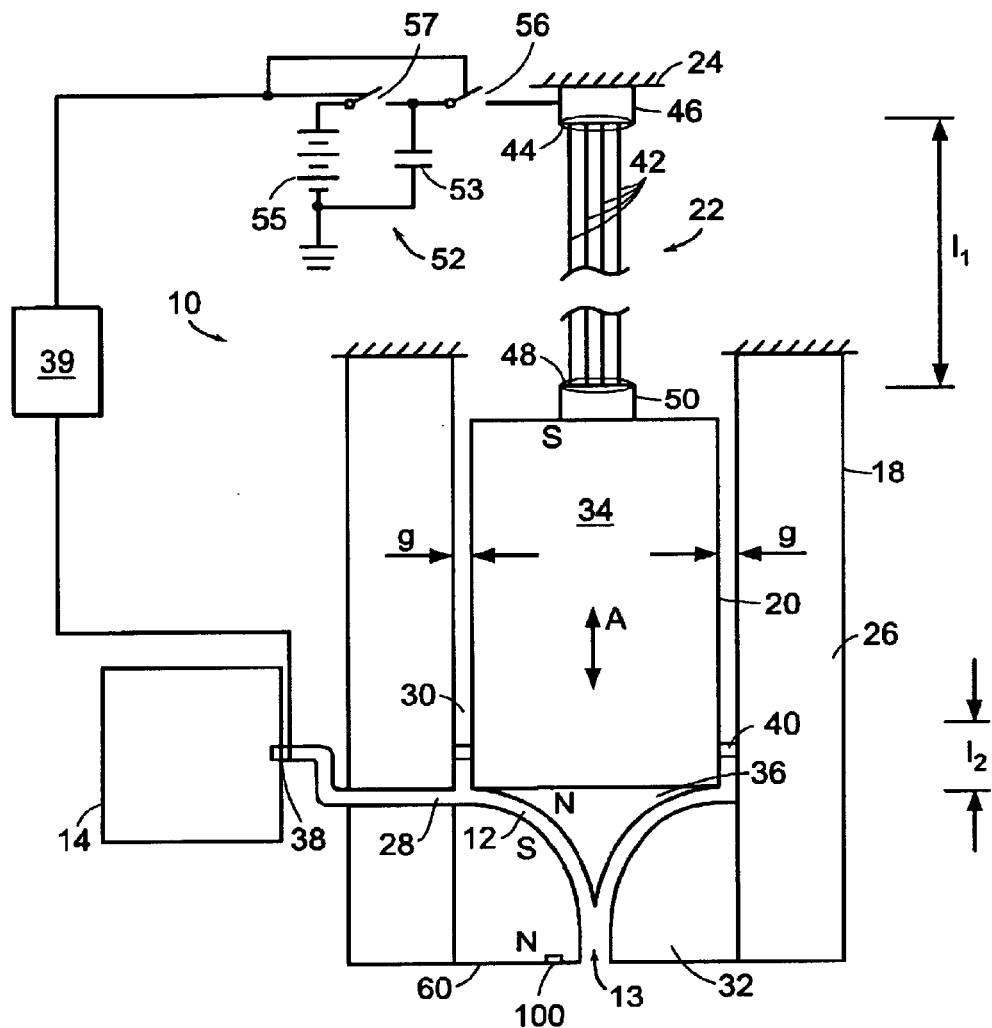
FIG. 1 is a side schematic view of a drug delivery device in accordance with the invention.

Referring to FIG. 1, there is shown a schematic view of a drug delivery device 10 which is used to inject a liquid formulation of an active principle such as, for example, a drug into a biological body such as a agriculture animal. The drug is initially contained in a chamber 12 of the device and is injected out through an orifice 13 into the animal. A drug reservoir 14 supplies the chamber 12 with sufficient amount of the drug for each injection and holds enough of the drug for approximately 20 to 200 or more injections. Alternatively, and particularly for use with humans, individual doses may be provided in a plurality of reservoirs sequentially coupled to the delivery device.

The device 10 includes a horn 18 in which a piston 20 is positioned. One end of an actuator 22 is attached to the piston 20, and the other end is attached to a surface 24. The surface 24 and the horn 18 are mounted in a manner, for example, within an applicator, such that the piston 20 is able to move back and forth in the direction of the double arrow A relative to the horn 18 and the surface 24.

The horn 18 includes an outer housing 26 provided with an inlet port 28, a bore 30, and a tapered section 32. The piston 20 includes a cylindrical section 34 spaced apart from the inner surface of the bore 30 by a narrow gap, g, such as 50 μm to 250 μm, preferably 100 μm, to form a clearance seal, and an end section 36 having the same shape as the tapered section 32 of the horn 18. The end section 36 of the piston and the tapered section 32 of the horn define the chamber 12 which receives a desired amount of the drug from the reservoir 14 through the inlet port 28. A valve 38 is located within the inlet port 28, or between the port and the reservoir 14, and is opened and closed under the direction of a controller 39, such as, for example, a microprocessor, to allow the desired amount of drug into the chamber 12 for each injection. Additionally, there is a ring seal 40 to prevent the drug from escaping from the chamber 12 out between the horn 18 and the piston 20.

The actuator 22 includes one to 10 or more fibers 42 arranged parallel to one another. One end 44 of the fibers 42 is attached to the surface 24 with a clamp 46 and the other end 48 is attached to the piston 20 with another clamp 50 so that the fibers 42 are under tension. Each of the fibers 42 is insulated from the other fibers along its length by an insulating coating. Further, the ends 48 are insulated from each other in the clamp 50, whereas the ends 44 are in electrical contact with each other through the clamp 46. When a potential is applied to the ends 44, the fibers 42 contract to move the piston 20 away from the horn 18.

A class of materials that contact when a potential is applied to them includes piezoelectric crystals and shape memory alloys. While piezoelectric crystals contract about 1%, shape memory alloys are able to contract approximately 5%. The larger contraction of shape memory alloys make them desirable for the illustrated embodiment. Accordingly, the fibers 42 are made of a shape memory alloy such as, for example, Ni—Ti available under the Trade Mark Nitinol.

When a potential from a power source 52, also under the direction of the controller 39, is applied to the ends 44 of the fibers 42 the fibers heat up. As the fibers heat up, a phase transformation of the fiber material occurs, namely, the fiber changes from martensite to austenite. This phase transformation causes the fibers 42 to contract such that the piston 20 is pulled way from the horn 18. A more detailed description of shape memory alloys and their use is described in U.S. Pat. No. 5,092,901, the contents of which are incorporated herein in its entirety.

In the presently discussed embodiment, the piston 20 and the tapered section 32 of the horn 18 are permanent magnets such that the facing surfaces of the tapered section 32 and the end section 36 are oppositely polarized. Magnetic forces bring the horn and the piston rapidly together when the potential is removed to allow the fibers 42 to relax. Because the magnetic force is inversely related to the square of the distance between the surfaces, the force rapidly increases through the stroke. By using permanent magnets rather than electromagnets, the large mass and power requirements of an electromagnet are avoided, although in some other embodiments, electromagnets are used. Also, in some embodiments, the tapered section 32 is a metal rather than a permanent magnet.

The power source 52 includes a super capacitor 53 that is energized by a set of batteries 55. Accordingly, the potential is applied to the fibers 42 when the super capacitor 53 discharges though a closed switch 56, and is removed when the super capacitor is being recharged with the batteries 55. The power source 52 is also provided with an on/off switch 57. Although any capacitor can be used to apply a potential to the fibers 42 when the capacitor discharges, a super capacitor has the advantageous feature of providing a large energy density in a small physical size. The super capacitor 53 has a volume from 1.5 ml to 30 ml, preferably 3 ml, and an energy output of 10 J to 1 KJ, preferably 100 J. The current applied to the fibers 42 is approximately 100 mAmps to 5 Amps, and the voltage applied to the fibers is between about 1 volt to 10 volts. In one embodiment, the applied current is 1 Amp, and the applied voltage is 5 volts.

The fibers 42 have a length, $l_1$, of approximately 10 mm to 200 mm, preferably 100 mm that when contracted pulls the piston 20 from the horn 18 by a distance, $l_2$, of approximately 0.5 mm to 10 mm, preferably 5 mm. The fibers 42 can have circular cross section, in which case each fiber 42 has a diameter of approximately 0.025 mm to 2 mm. Alternatively, each fiber can have a flat ribbon shape with a thickness approximately in the range 0.025 mm to 0.5 mm and a width of approximately 0.75 mm to 10 mm. Other suitable shape memory alloys include Ag—Cd, Au—Cd, Au—Cu—Zn, Cu—Al, Cu—Al—N, Cu—Zn, Cu—Zn—Al, Cu—Zn—Ga, Cu—Zn—Si, Cu—Zn—Sn, Fe—Pt, Fe—Ni, In—Cd, In—Ti, Ti—Nb, and Ti—Ni.

Figure 2A:
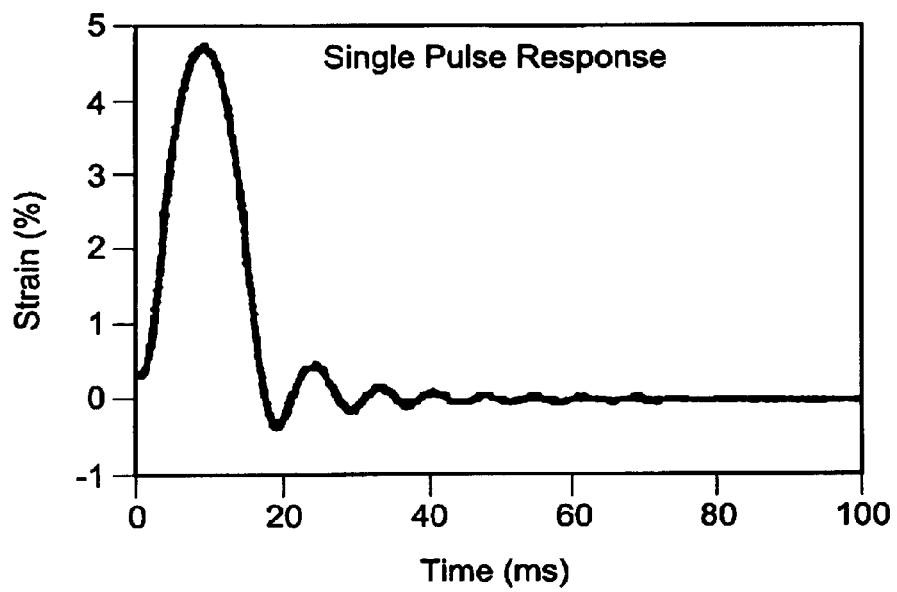
FIG. 2A is a graph of the time response of a shape memory alloy actuator of the drug delivery device of FIG. 1 for a high strain.
Figure 2B:
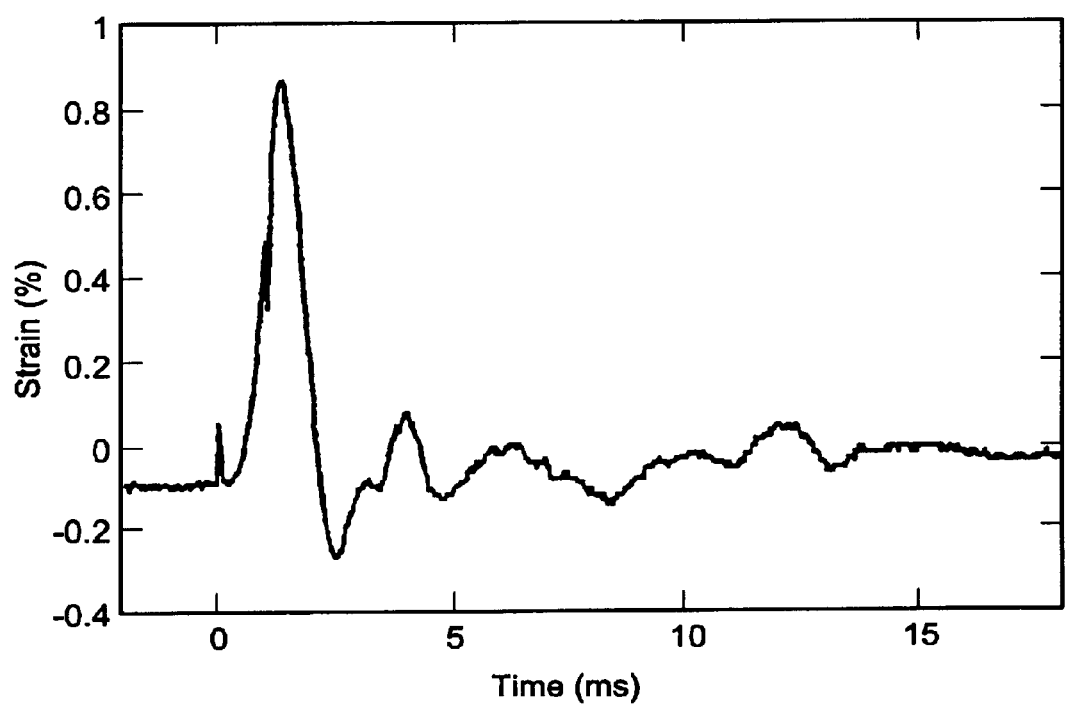
FIG. 2B is a graph of the time response of the shape memory alloy actuator when the actuator is subjected to a potential as a quick pulse.

Referring to FIGS. 2A and 2B, there are shown graphs of the time response of the fibers 42 made from NiTi. Shown in FIG. 2A is the response of a fiber subjected to a strain of nearly 5%. As can be seen, the contraction time for this fiber is about 10 ms. By way of contrast, FIG. 2B illustrates a fiber subjected to faster pulse than that applied to the fiber of FIG. 2A. With the faster pulse, the fiber experiences a strain of about 1%, while the contraction time is about 1 ms.

In use, the device 10 is typically mounted within applicator that is held by an operator. The applicator is shaped as a pistol, cylinder or any other suitable geometry. Before the operator activates the device 10, magnetic forces hold the piston 20 and the horn 18 together in a manner such that the end section 36 of the piston 20 is seated and in contact with the tapered section 32 of the horn 18.

The operator positions the applicator such that a surface 60 of the horn 18 is placed against the skin of an animal such as a pig and turns on the device 10 with the switch 57. The operator then triggers the device 10 such that the controller 38 closes the switch 56 to allow the super capacitor 53 to discharge thereby applying a potential to the fibers 42 which causes them to contract. Hence, as the fibers 42 contract they pull the piston 20 away from the horn 18 to define the chamber 12 between the tapered section 32 of the horn and the end section 36 of the piston. The controller 39 simultaneously instructs the valve 38 to open to allow the drug to flow from the reservoir 14 through the inlet port 28 into the chamber 12. After a prescribed period of time, the controller 39 directs the valve 38 to close so that a desired amount of the drug is held in the chamber 12 for a single injection.

Next, the switch 56 is opened so that the as the batteries 55 recharge the super capacitor 53, the potential to the fibers 42 is withdrawn, and the fibers 42 relax. As this occurs, because of the magnetic attraction between the horn 18 and the piston 20, the end section 36 of the piston 20 accelerates towards the tapered section 32. As the end section 36 and the tapered section 32 come closer together, the volume of the chamber 12 is reduced thereby expelling the drug from the chamber 12 through the orifice 13 into the skin. Note that as the end section 36 and the tapered section 32 come together, the injection pressure applied to the drug through the orifice 13 increases since the speed at which end section 36 moves toward the tapered section 32 increases inversely with the square of the distance between the two. In addition, the particular shape of the tapered section 32 narrows down the acoustic wave to provide higher amplification. The injection pressure is at least 1 MPa and can be as high as 300 MPa.

The batteries 55 recharge the super capacitor 53 for the next injection, while the operator removes the applicator from the animal and begins the process with a new animal. In the present application, the reservoir 14 contains enough of the drug for about 100 to 200 injections. When the reservoir 14 is depleted, the operator picks up another applicator to continue with the process. Alternatively, the reservoir 14 can be a removable cartridge that the operator easily exchanges with another cartridge filled with the drug.

While this invention has been particularly shown and described with references to preferred embodiments thereof, it will be understood by those skilled in the art that various changes in form and details may be made therein without departing from the scope of the invention encompassed by the appended claims. For example, in an alternative embodiment, the horn 18 is provided with a pressure or force sensor 100 (FIG. 1) so that the entire injection process described above is automatically triggered. In such an implementation, the operator merely places the surface 60 of the horn 18 against the skin and when the sensor 100 detects that there is an appropriate contact force or pressure between the skin and the surface 60, the device 10 is triggered to inject the drug into the animal and subsequently re-cocks or re-loads for the next animal. In yet another alternative embodiment, contractile polymers, or any other suitable contracting material, can be used instead of the shape memory alloy.

What is claimed is:

1. An injector, comprising:
    a housing having a chamber for holding a liquid formulation of an active principle to be injected into a biological body and an output port in fluid communication with the chamber, the liquid fomulation being injected through the output port;
    a piston positioned within the housing, the piston including an end portion with substantially the same shape as the chamber; and
    an actuator attached to the piston and adapted to force the piston away from the housing in opposition to a magnetic force, the piston and housing being drawn together by a magnetic force in response to the actuator relaxing its force on the piston to expel the liquid formulation out of the chamber through the output port.

2. The injector of claim 1 further comprising an inlet port for filling the chamber with the liquid formulation.

3. The injector of claim 1 wherein the actuator is made of a shape memory alloy, the actuator moving the piston away from the housing when a potential is applied to the actuator, and the piston moving towards the housing when the voltage is removed.

4. The injector of claim 3 wherein the actuator is one or more fibers of the shape memory alloy.

5. The injector of claim 3 wherein the shape memory alloy is Ni—Ti.

6. The injector of claim 3 wherein the shape memory alloy is approximately 10 mm to 200 mm long.

7. The injector of claim 6 wherein the shape memory alloy contracts approximately 0.5 mm to 10 mm when the potential is applied to the alloy.

8. The injector of claim 3 wherein the shape memory alloy structure changes phase from martensite to austenite when the potential is applied to the alloy.

9. The injector of claim 3 further comprising a capacitor, wherein the potential is applied to the actuator when the capacitor discharges.

10. The injector of claim 9 wherein the capacitor has an energy output of about 100 J.

11. The injector of claim 9 wherein the capacitor has an energy output of at least about 10 J.

12. The injector of claim 1 wherein the injector has a maximum injection pressure of approximately 300 MPa.

13. The injector of claim 1 wherein the injector has an injection pressure of at least 1 Mpa.

14. The injector of claim 1 wherein the injector has a cycle time of about one sec.

15. The injector of claim 1 wherein the output port has a diameter of about 50 $\mu$m to 200 $\mu$m.

16. The injector of claim 1 wherein the chamber has a tapered shape.

17. The injector of claim 1 wherein the liquid formulation is a drug.

18. The injector of claim 1 further comprising an actuator attached to the piston and made of contractile polymers, the actuator moving the piston away from the housing when a potential is applied to the actuator, and the piston moving towards the housing when the voltage is removed.

19. The injector of claim 1 further comprising an actuator attached to the piston and made of a contracting material, the actuator moving the piston away from the housing when a potential is applied to the actuator, and the piston moving towards the housing when the voltage is removed.

20. An injector, comprising:
    a housing having a chamber for holding a liquid formulation of an active principle to be injected into a biological body and an output port in fluid communication with the chamber, the liquid formulation being injected though the output port;
    a piston positioned within the housing, the piston including an end portion with substantially the same shape as the chamber; and an actuator attached to the piston and made of shape memory alloy, the piston and housing being drawn together by a magnetic force, the actuator moving the piston away from the housing when a potential is applied to the actuator, and the piston moving towards the housing when the voltage is removed to expel the liquid formulation out of the chamber through the output port.

21. An injector, comprising:

a housing having a chamber for holding a liquid formulation of an active principle to be injected into a biological body and an output port in fluid communication with the chamber, the liquid formulation being injected through the output port; and a piston positioned within the housing, the piston including an end portion with substantially the same shape as the chamber, the piston and housing being drawn together by a magnetic force to expel the liquid formulation out of the chamber through the output port; and an actuator attached to the piston and made of shape memory alloy, the actuator moving the piston away from the housing when a potential is applied to the actuator, and the piston moving towards the housing when the voltage is removed.

22. The injector of claim 21 wherein the actuator is one or mare fibers of the shape memory alloy.

23. The injector of claim 21 wherein the shape memory alloy is Ni—Ti.

24. The injector of claim 21 wherein the shape memory alloy is approximately 10 mm to 200 mm long.

25. The injector of claim 24 wherein the shape memory alloy contracts approximately 0.5 mm to 10 mm when the potential is applied to the alloy.

26. The injector of claim 21 wherein the shape memory alloy structure changes phase from martensite to austenite when the potential is applied to the alloy.

27. The injector of claim 21 further comprising a capacitor, wherein the potential is applied to the actuator when the capacitor discharges.

28. The injector of claim 27 wherein the capacitor has an energy output of about 100 J.

29. The injector of claim 27 wherein the capacitor has an energy output of at least about 10 J.

30. An injector, comprising:

a housing having a chamber for holding a liquid formulation of an active principle to be injected into a biological body and an output port in fluid communication with the chamber, the liquid formulation being injected through the output port;

a piston positioned within the housing, the piston including an end portion with substantially the same shape as the chamber; and an actuator attached to the piston and made of contractile polymers, the actuator moving the piston away from the housing when a potential is applied to the actuator, and the piston moving towards the housing when the voltage is removed, the piston and housing being drawn together by a magnetic force to expel the liquid formulation out of the chamber through the output port.

31. An injector, comprising:

a housing having a chamber for holding a liquid formulation of an active principle to be injected into a biological body and an output port in fluid communication with the chamber, the liquid formulation being injected through the output port;

a piston positioned within the housing, the piston including an end portion with substantially the same shape as the chamber; and an actuator attached to the piston and made of a contracting material, the actuator moving the piston away from the housing when a potential is applied to the actuator, and the piston moving towards the housing when the voltage is removed, the piston and housing being drawn together by a magnetic force to expel the liquid formulation out of the chamber through the output port.

32. The injector of claim 1, wherein the magnetic force is supplied by a permanent magnet.

* * * * *